United States Patent
Cohen Evenram et al.

(10) Patent No.: US 9,243,225 B2
(45) Date of Patent: Jan. 26, 2016

(54) METHODS OF OBTAINING CELL POPULATIONS ENRICHED WITH DESIRED CELLS

(75) Inventors: Sharona Cohen Evenram, Jerusalem (IL); Benjamin Reubinoff, Moshav Bar-Giora (IL)

(73) Assignee: HADASIT MEDICAL RESEARCH SERVICES & DEVELOPMENT LIMITED, Jerusalem (IL)

( * ) Notice: Subject to any disclaimer, the term of this patent is extended or adjusted under 35 U.S.C. 154(b) by 0 days.

(21) Appl. No.: 13/825,602

(22) PCT Filed: Sep. 27, 2011

(86) PCT No.: PCT/IL2011/000762
§ 371 (c)(1),
(2), (4) Date: Jun. 11, 2013

(87) PCT Pub. No.: WO2012/042519
PCT Pub. Date: Apr. 5, 2012

(65) Prior Publication Data
US 2013/0280218 A1    Oct. 24, 2013

Related U.S. Application Data

(60) Provisional application No. 61/386,691, filed on Sep. 27, 2010.

(51) Int. Cl.
*A01N 1/02* (2006.01)
*C12N 5/0793* (2010.01)
*C12N 5/0797* (2010.01)
*A61K 31/337* (2006.01)
*A61K 47/48* (2006.01)
*A61K 39/395* (2006.01)

(52) U.S. Cl.
CPC ............ *C12N 5/0619* (2013.01); *C12N 5/0623* (2013.01); *A61K 31/337* (2013.01); *A61K 39/39558* (2013.01); *A61K 47/4863* (2013.01); *A61K 47/48584* (2013.01); *C12N 2501/06* (2013.01); *C12N 2501/115* (2013.01); *C12N 2501/119* (2013.01); *C12N 2501/13* (2013.01); *C12N 2501/15* (2013.01); *C12N 2501/999* (2013.01)

(58) Field of Classification Search
CPC ........... A61K 39/39558; A61K 31/337; A61K 47/48584; A61K 47/4863; C07K 16/30; C12Q 1/6886
USPC ....................................................... 424/93.7
See application file for complete search history.

(56) References Cited

FOREIGN PATENT DOCUMENTS

| EP | 1 930 412 A1 | 6/2008 |
|---|---|---|
| WO | 03/018767 A2 | 3/2003 |
| WO | 03/104444 A1 | 12/2003 |

OTHER PUBLICATIONS

Rosettes. The four main types of rosettes in pathology. Pathology Student. 2012;1-2.*
Carpenter, et al., "Characterization and Differentiation of Human Embryonic Stem Cells", Cloning and Stem Cells, vol. 5, No. 1, pp. 79-88, (2003).
The International Search Report for International Application No. PCT/IL2011/000762, five pages, mailed Feb. 15, 2012.
Amariglio, et al., "Donor-Derived Brain Tumor Following Neural Stem Cell Transplantation in an Ataxia Telangiectasia Patient", PLoS Med, vol. 6, Issue 2, e1000029, pp. 0221-0231, (2009).
Cho, et al., "Highly efficient and large-scale generation of functional dopamine neurons from human embryonic stem cells", PNAS, vol. 105, No. 9, pp. 3392-3397, (2008).
Hedlund, et al., "Selection of Embryonic Stem Cell-Derived Enhanced Green Fluorescent Protein-Positive Dopamine Neurons Using the Tyrosine Hydroxylase Promoter Is Confounded by Reporter Gene Expression in Immature Cell Populations", Stem Cells, vol. 25, No. 5, pp. 1126-1135, (2007).
Iacovitti, et al., "A protocol for the differentiation of human embryonic stem cells into dopaminergic neurons using only chemically defined human additives: Studies in vitro and in vivo", Brain Research, vol. 1127, No. 1, pp. 19-25, (2007).
Lee, et al., "Directed Differentiation and Transplantation of Human Embryonic Stem Cell-Derived Motoneurons", Stem Cells, vol. 25, No. 8, pp. 1931-1939, (2007).
Thinyane, et al., "Fate of pre-differentiated mouse embryonic stem cells transplanted in unilaterally 6-hydroxydopamine lesioned rats: Histological characterization of the grafted cells", Brain Research, vol. 1045, Nos. 1-2, pp. 80-87, (2005).
Goldman et al., "Reply: Large stem cell grafts could lead to erroneous interpretations of behavioral results?" Nature Medicine, vol. 13, No. 2, pp. 118-119, (2007).
Hedlund, et al., "Embryonic Stem Cell-Derived Pitx3-Enhanced Green Fluorescent Protein Midbrain Dopamine Neurons Survive Enrichment by Fluorescence-Activated Cell Sorting and Function in an Animal Model of Parkinson's Disease", Stem Cells, vol. 26, No. 6, pp. 1526-1536, (2008).

(Continued)

*Primary Examiner* — Renee Claytor
*Assistant Examiner* — Lynn Y Fan
(74) *Attorney, Agent, or Firm* — Vorys, Sater, Seymour and Pease LLP

(57) ABSTRACT

Provided is a method including providing a population of cells including a target type of differentiated cells having a pre-identified cytoskeletal profile and at least one cell selected from undifferentiated cells, differentiating cells and differentiated cells being different from the target type of differentiated cells; and incubating the population of cells with a cytotoxic agent, in an amount and for a time period effective to form a modified population of cells including predominantly or consisting essentially of the target type of differentiated cells. The pre-identified cytoskeletal profile can include the presence of class III β-tubulin on neuronal cells and the population of cells includes neural cells and neuronal cells.

10 Claims, 4 Drawing Sheets

(56) References Cited

OTHER PUBLICATIONS

Cai, et al., "The Role of Lmx1a in the Differentiation of Human Embryonic Stem Cells into Midbrain Dopamine Neurons in Culture and After Transplantation into a Parkinson's Disease Model", Stem Cells, vol. 27, No. 1, pp. 220-229, (2009).

Haggarty, et al., "Domain-selective small-molecule inhibitor of histone deacetylase 6 (HDAC6)-mediated tubulin deacetylation", PNAS, vol. 100, No. 8, pp. 4389-4394, (2003).

Fanarraga, et al., "Expression of unphosphorylated class III β-tubulin isotype in neuroepithelial cells demonstrates neuroblast commitment and differentiation", European Journal of Neuroscience, vol. 11, No. 2, pp. 517-527, (1999).

Hari, et al., "Expression of Class III β-Tubulin Reduces Microtubule Assembly and Confers Resistance to Paclitaxel", Cell Motility and the Cytoskeleton, vol. 56, No. 1, pp. 45-56, (2003).

Lariviere, et al., "Functions of Intermediate Filaments in Neuronal Development and Disease", J Neurobiol, vol. 58, No. 1, pp. 131-148, (2004).

Lendahl, et al., "CNS Stem Cells Express a New Class of Intermediate Filament Protein", Cell, vol. 60, No. 4, pp. 585-595, (1990).

Steinert, et al., "Molecular Parameters of Type IV α-Internexin and Type IV-Type III α-Internexin-Vimentin Copolymer Intermediate Filaments", J. Biol. Chem., vol. 274, No. 3, pp. 1657-1666, (1999).

Bargagna-Mohan, et al., "The Tumor Inhibitor and Antiangiogenic Agent Withaferin A Targets the Intermediate Filament Protein Vimentin", Chemistry & Biology, vol. 14, No. 6, pp. 623-634, (2007).

Allegrucci, et al., "Differences between human embryonic stem cell lines", Human Reproduction Update, vol. 13, No. 2, pp. 103-120, (2007).

Noggle, et al., "A Molecular Basis for Human Embryonic Stem Cell Pluripotency", Stem Cell Reviews, vol. 1, No. 2, pp. 111-118, (2005).

Deb, et al., "Embryonic Stem Cells: From Markers to Market", Rejuvenation Research, vol. 11, No. 1, pp. 19-38, (2007).

Hoffman, et al., "Characterization and culture of human embryonic stem cells", Nature Biotechnology, vol. 23, No. 6, pp. 699-708, (2005).

Kiskinis, et al., "Progress toward the clinical application of patient-specific pluripotent stem cells", The Journal of Clinical Investigation, vol. 120, No. 1, pp. 51-59, (2010).

Li, et al. "Small molecules that modulate embryonic stem cell fate and somatic cell reprogramming", Trends in Pharmacological Sciences, vol. 31, No. 1, pp. 36-45, (2009).

Shao, et al., "Gene-delivery systems for iPS cell generation", Expert Opin Biol Ther., vol. 10, No. 2, pp. 231-242, (2010).

Turetsky, et al., "Laser-assisted derivation of human embryonic stem cell lines from IVF embryos after preimplantation genetic diagnosis", Human Reproduction, vol. 23, No. 1, pp. 46-53, (2008).

Thomson, et al., "4. Primate Embryonic Stem Cells", Current Topics in Developmental Biology, vol. 38, pp. 133-165, (1998).

Bongso, et al., "Isolation and culture of inner cell mass cells from human blastocysts", Human Reproduction, vol. 9, No. 11, pp. 2110-2117, (1994).

Klimanskaya, et al., "Human embryonic stem cell lines derived from single blastomeres", Nature, vol. 444, No. 7118, pp. 481-485, (2006). Correction & Amendment, Nature, vol. 446, p. 342, (2007).

Kim, et al., "Sonic hedgehog and FGF8 collaborate to induce dopaminergic phenotypes in the Nurr1-overexpressing neural stem cell", Biochemical and Biophysical Research Communications, vol. 305, No. 4, pp. 1040-1048, (2003).

Forsyth, et al., "Phorboxazole Analogues Induce Association of cdk4 with Extranuclear Cytokeratin Intermediate Filaments", J. Am. Chem. Soc., vol. 128, No. 12, pp. 3858-3859, (2006).

Cohen, et al., "Neural Differentiation of Human ES Cells", Curr. Protoc. Cell Biol., vol. 36, Chapter 23, Unit 23.7, pp. 23.7.1-23.7.20, (2007).

Vierbuchen, et al., "Direct conversion of fibroblasts to functional neurons by defined factors", published as Nature, vol. 463, No. 7284, pp. 1035-1041, (2010), 19 pages.

Bieberich, et al., "Selective apoptosis of pluripotent mouse and human stem cells by novel ceramide analogues prevents teratoma formation and enriches for neural precursors in ES cell-derived neural transplants", The Journal of Cell Biology, vol. 167, No. 4, pp. 723-734, (2004).

Chung, et al., "Genetic selection of sox1GFP-expressing neural precursors removes residual tumorigenic pluripotent stem cells and attenuates tumor formation after transplantation", Journal of Neurochemistry, vol. 97, No. 5, pp. 1467-1480, (2006).

Ferreira, et al., "Expression of the Class III β-Tubulin Isotype in Developing Neurons in Culture", Journal of Neuroscience Research, vol. 32, pp. 516-529, (1992).

Gerrard, et al., "Differentiation of Human Embryonic Stem Cells to Neural Lineages in Adherent Culture by Blocking Bone Morphogenetic Protein Signaling", Stem Cells, vol. 23, pp. 1234-1241, (2005).

Horwitz, "TAXOL* (paclitaxel): Mechanisms of actions", Annals of Oncology, vol. 5, (Suppl. 6), pp. 83-86, (1994).

Itsykson, et al., "Derivation of neural precursors from human embryonic stem cells in the presence of noggin", Mol. Cell. Neurosci., vol. 30, No. 1, pp. 24-36, (2005).

Li, et al., "Critical issues of clinical human embryonic stem cell therapy for brain repair", Trends in Neurosciences, vol. 31, No. 3, pp. 146-153 (2007).

Mozzetti, et al., "Class III β-Tubulin Overexpression Is a Prominent Mechanism of Paclitaxel Resistance in Ovarian Cancer Patients", Clin Cancer Res, vol. 11, pp. 298-305, (2005).

Reubinoff, et al., "Neural progenitors from human embryonic stem cells", Nature Biotechnology, vol. 19, No. 12, pp. 1134-1140, (2001).

Schuldiner, et al., "Selective Ablation of Human Embryonic Stem Cells Expressing a 'Suicide' Gene", Stem Cells, vol. 21, No. 3, pp. 257-265, (2003).

Tommasi, et al., "Cytoskeleton and paclitaxel sensitivity in breast cancer: The role of β-tubulins", Int. J. Cancer, vol. 120, No. 10, pp. 2078-2085, (2007).

* cited by examiner

Figure 1A
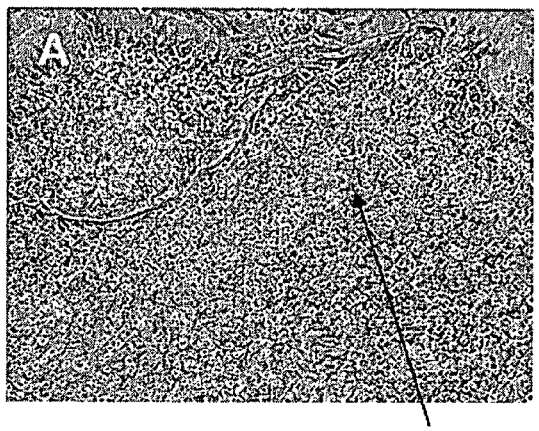
Large colony of undifferentiated hESC
Figure 1B
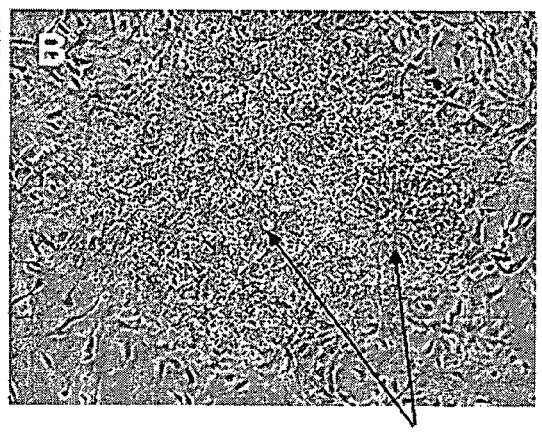
neural rosettes (very early progenitors)
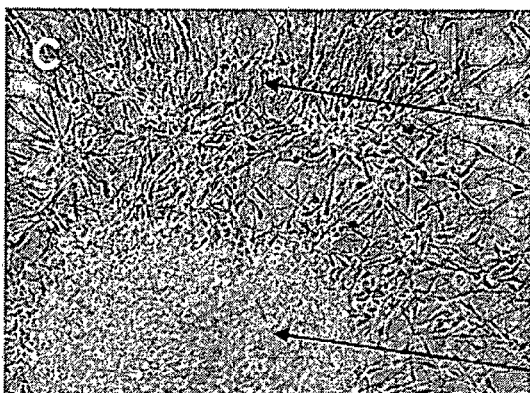
Unaffected neuronal cells
Apoptotic cells
Figure 1C Figure 2A
Figure 2B
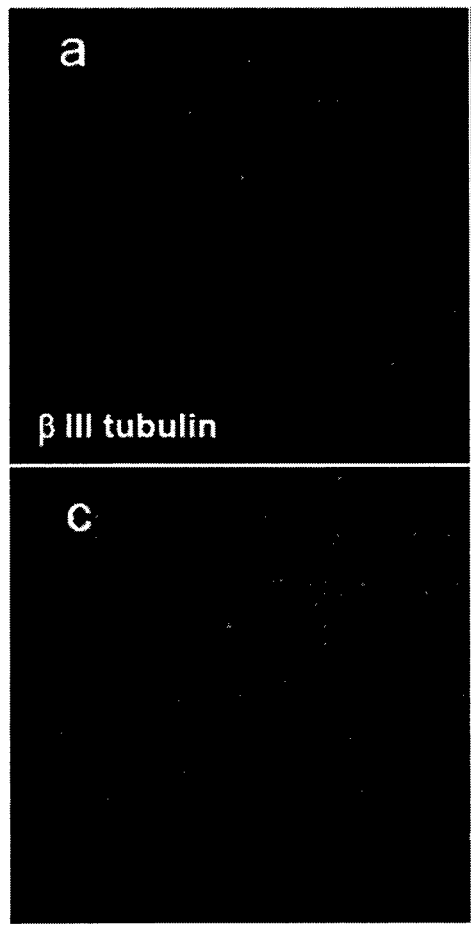
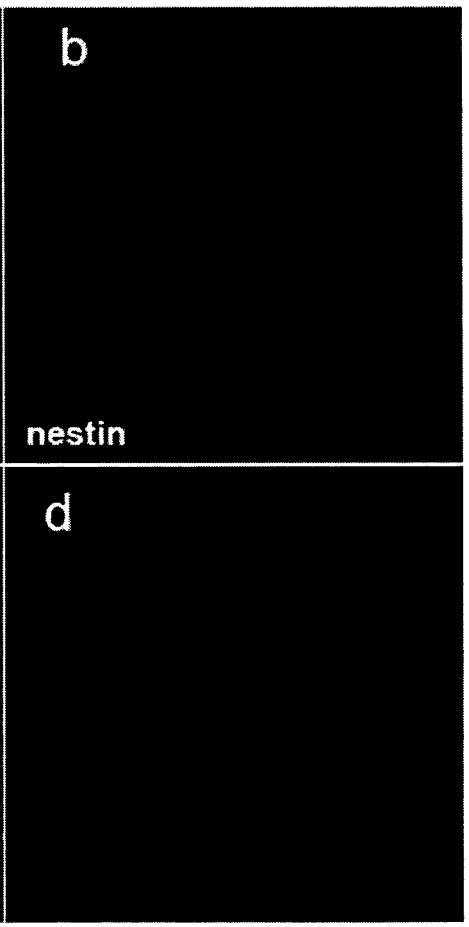
Figure 2C
Figure 2D Figure 3A  Figure 3B  Figure 3C
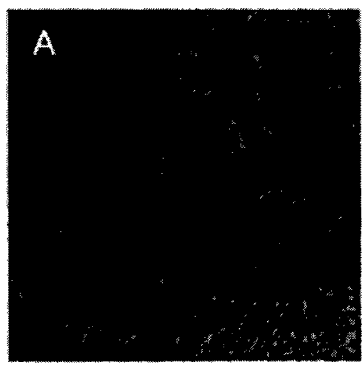 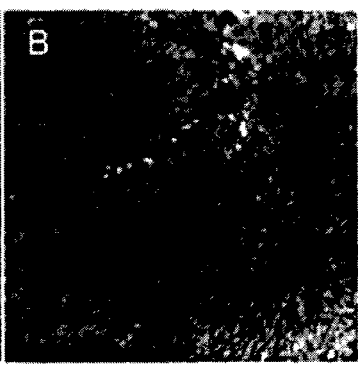 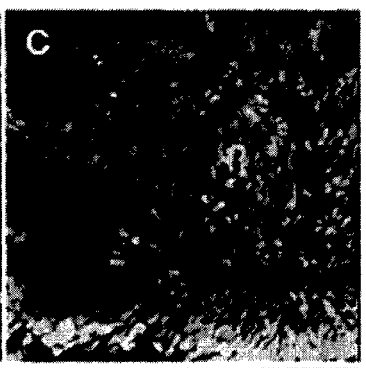
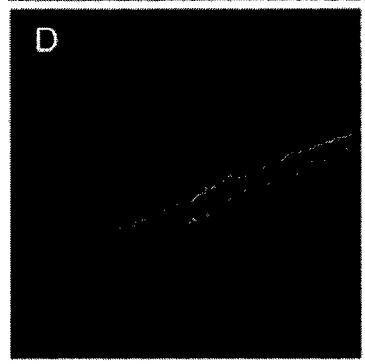 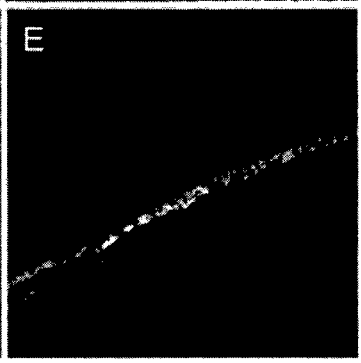 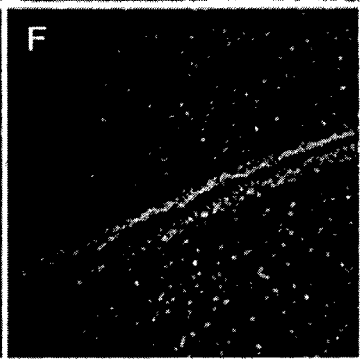
Figure 3D  Figure 3E  Figure 3F

METHODS OF OBTAINING CELL POPULATIONS ENRICHED WITH DESIRED CELLS

FIELD OF THE INVENTION

This invention relates to methods for obtaining from stem cells, cell population enriched with a desired cell type, e.g. with dopaminergic cells.

BACKGROUND OF THE INVENTION

Regenerative cell therapy of the nervous system is an emerging promising mode to of therapy. Pluripotent stem cells such as human embryonic stem cells (hESCs) or induced pluripotent stem (iPS) cells may serve as an unlimited source of neurons for transplantation into the nervous system. However, transplantation of pluripotent stem cells-derived neurons may be complicated by the presence of contaminating undesired cells within the transplanted neuronal population. These undesired (contaminating) cells may give rise to the formation of teratoma tumors, and tumors comprised of proliferating neural precursors/progenitors (NPs). In addition, the undesired cells may be the origin of undesired, non-neuronal, cells within the grafts such as neural precursors, non-neural cells or tissues, as well as various glial cells such as astrocytes, microglia or oligodendroglial cells.

Human adult neural stem cells (NSCs) or progenitor cells derived from the brain of aborted fetuses or post natal brain at any age may serve as a source of neurons for transplantation therapy. Nevertheless, transplantation of neurons derived from such cells may also be complicated by the presence of contaminating cells within the transplanted neuronal population. These contaminating cells may also give rise to the formation of tumors comprised of proliferating NSCs or neural precursors/progenitors (NPs)[1], and to the presence of unwanted non-neuronal cells within the graft such as NSCs &NPs, as well as various glial cells such as astrocytes, microglia or oligodendroglial cells.

Parkinson's disease is one example of a condition that may be treated with cell therapy. However, complications that can arise due to the presence of unwanted cells within neuron transplants. Specifically, cell transplantation of dopaminergic (DA) neurons is an attractive therapeutic approach for Parkinsonism, aiming towards restoration of the DA innervations in the affected striatum. Transplantation of fetal mesencephalic tissue in humans showed improvements in some patients. However limited availability of fetal tissue and ethical issues stress the need for alternatives. hESCs may serve as an inexhaustible resource for DA neurons. Several groups have developed and perfected various protocols for derivation of DA neurons from pluripotent stem cells[2][3-5]. Yet, teratoma and neural tumor formation by pluripotent cells and proliferative NPs was demonstrated after transplantation of hESC-derived progeny into animal models of Parkinson's disease[6, 7]. These hurdles impede any prospective clinical use of such cells.

Several strategies have been employed so far to avoid teratoma, neural tumor formation, and the existence of unwanted cells within transplanted cell population including, negative and positive selection methods using fluorescence-activated cell sorting (FACS), magnet activated cell sorting (MACS), and immuno-panning all of which require labeling of cell-surface markers for live cell selection. However, specific cell surface markers for labeling desired cell types may not be available or known. For example, in the case of selecting DA neurons for transplantation in Parkinson's disease, a DA neuron-specific cell surface marker has not been identified yet.

To overcome the above problem, genetically modified cell lines have been used. For example, cells expressing green fluorescent protein (GFP) or antibiotics resistance driven by tyrosine hydroxylase (TH)[3] or PitX3[8] promoters that enable antibiotics selection or FACS sorting of transgene-expressing cells were developed for the selection of DA neurons for transplantation in animal models of Parkinson's disease.

Another strategy to enrich for a desired neuronal subtype, which is also based on genetic modification, is forced expression of transcription factors which have a key role during embryonic development of the desired neuronal subtype. For example, Lmx1a in human neural progenitors promotes DA neuron differentiation[9]. However, the above enrichment and selection methods require genetic modification of the cells and therefore are less likely to be clinically applied.

An additional promising application of stem cells is their utilization for drug discovery, and screening of compounds for potential differentiation, survival, therapeutic, teratogenic or toxic effects. Both human ESCs and iPS cells may be utilized to model diseases. For example, human ESCs derived from preimplantation diagnosed affected embryos are used to model the inherited disease that they carry. Human ESCs may be genetically modified to model genetic disorders. Human iPS cells may be derived from patients with both inherited diseases as well as disease of unknown/multifactorial etiology. Differentiated neurons derived from theses pluripotent stem cell models may serve to model the pathogenesis of neural disorders and for the development of new drugs. However, the neuronal cells that are obtained after spontaneous or induced differentiation of pluripotent stem cells are contaminated by undifferentiated stem cells, non-neural cells, neural precursors and glia cells. These contaminating cells interfere with the utilization of the neurons for studying the pathogenesis of neural disorders, drug discovery, including high throughput screening of compounds for neuroprotective and/or therapeutic effect.

An alternative source for neurons may be transdifferentiation of somatic cells by forced expression of transcription factors. Fibroblasts could be converted by this approach to various types of neuronal cells[33].

Neurons that are generated through transdifferentiation may be utilized for multiple applications including toxicology, drug discovery, basic research and cell therapy. Nevertheless, the neurons that are obtained following transdifferentiation are mixed with non-neuronal cells such as the somatic cells of origin and others. The presence of contaminating non-neuronal cells interferes with the use of the trans-differentiated neurons for the various applications.

SUMMARY OF THE INVENTION

The present invention provides a method for obtaining a population of cells enriched with, or predominantly consisting of differentiated cells that exhibit a pre-identified cytoskeletal profile. The profile defines resistance of the differentiated cells to a cytotoxic agent.

In one particular embodiment, the cytotoxic agent is an apoptosis inducing agent and the method of the invention induces selective death of cells in the cell population that are sensitive to the apoptosis inducing agent, thus, maintaining only cells that exhibit the pre-identified cytoskeletal profile The pre-identified cytoskeletal profile encompasses the existence of absence of a cytoskeletal component.

The cytoskeletal component according to the invention may be, without being limited thereto, class III β-tubulin, the presence thereof (defining the desired and pre-identified cytoskeletal profile) providing the cells with resistance to treatment with a cytotoxic agent.

In one preferred embodiment, the cytotoxic agent is a microtubule-stabilizing agent such as microtubule-stabilizing taxanes, including paclitaxel and docetaxel, to which the desired cell population are resistant (e.g. due to the expression of class III β-tubulin).

In another preferred embodiment, the cytoskeletal component is vimentin, the absence thereof (defining the desired and pre-identified cytoskeletal profile) providing the cells with resistance to treatment with, for example, withaferin A.

In accordance with the above, the present invention provides a method comprising:
  providing a population of cells comprising a target type of differentiated cells having a pre-identified cytoskeletal profile and at least one cell selected from the group consisting of differentiated cells being different from the target type of differentiated cells, undifferentiated stem cells and progenitor cells;
  incubating the population of cells with a cytotoxic agent in an amount and for a time period effective to form a modified population of cells comprising predominantly or consisting essentially of the target type of differentiated cells.

In one embodiment, the modified population of cells is enriched with or predominantly consists of a single type of differentiated cells. For example, the single type of differentiated cells may be neuronal cells that have a cytoskeletal profile including class III β-tubulin. The existence of class III β-tubulin in the cytoskeleton results in the differentiated cells being resistant to apoptosis inducing agents (the cytotoxic agent).

In some embodiments, the modified population of cells is enriched with or predominantly consists of a single type of cells selected from myocytes, such as cardiomyocytes; epithelial cells, such as retinal epithelial cells; blood cells; and bone cells, such as osteocytes.

The present disclosure also provides a population enriched with differentiated cells (essentially purified) that exhibit a pre-identified cytoskeletal profile (namely, that carry or lack a pre-identified cytoskeletal component).

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 1A-1C are images showing that paclitaxel selectively induces cell death of non-neuronal early differentiating and undifferentiated cells but does not affect mature neurons; specifically, FIGS. 1A and 1B show examples of undesired cells that appear in differentiating cultures; with arrows pointing to a large colony of undifferentiated cells in FIG. 1A and to neural rosettes that represent proliferating early neural precursors/progenitors (NPs) (FIG. 1B); FIG. 1C represents a paclitaxel-treated culture with a large cluster of apoptotic NPs (upper arrow) and adjacent unaffected neuronal cells (lower arrow).

FIGS. 2A-2D are fluorescence images showing a typical culture comprised of a mixture of neurons and NPs. FIGS. 2A-2B show immunostaining of the mixed culture for β-III tubulin (FIG. 2A; neurons) and for nestin (FIG. 2B; NPs) (βIII-tubulin-neuronal marker; nestin-NPs marker); compared to a similar culture after paclitaxel treatment (FIGS. 2C-2D) where the cell culture is enriched for β-III tubulin expressing cells (FIG. 2C), but has a reduced number of nestin-positive cells (FIG. 2D).

FIGS. 3A-3F are images showing that transplantation of treated cells (FIGS. 3D-3F) into a rat brain eliminates the formation of massive tumor formed after transplantation of untreated mixed culture cells (FIGS. 3A-3C).

DETAILED DESCRIPTION OF NON-LIMITING EMBODIMENTS

Figure 4A:
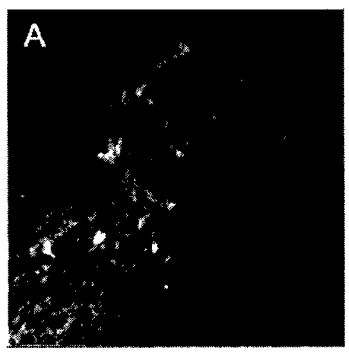
FIGS. 4A-4C are images showing that paclitaxel-treated grafted cells, marked by human nuclear antigen (HNA) (FIG. 4B), express tyrosine hydroxylase (TH) (FIG. 4A), a marker of dopaminergic neurons. Nuclear counterstaining with DAPI is presented in FIG. 4C.

The present invention is based on the understanding that there is a need in the art for methods of developing essentially purified populations of differentiated cells, such as neurons (e.g. dopaminergic), when produced from stem cells or by transdifferentiation from somatic cells.

Thus, there is provided a method comprising:
  providing a population of cells comprising a target type of differentiated cells having a pre-identified cytoskeletal profile and at least one cell selected from undifferentiated cells, differentiating cells and differentiated cells being different from the target type of differentiated cells;
  incubating the population of cells with a cytotoxic agent, in an amount and for a time period effective to form a modified population of cells comprising predominantly or consisting essentially of said target type of differentiated cells.

While the following description refers specifically to the production of a population of cells predominantly consisting of neural cells carrying class III β-tubulin, it should be understood that the invention also encompasses the production of essentially pure populations of other types of cells. The only criteria, according to the invention, is that the differentiated cells of interest (the "target type of differentiated cells") are characterized by a pre-identified cytoskeletal profile, that is used as a target for a cytotoxic agent. The cytoskeletal profile may be the presence or absence of a pre-defined cytoskeletal component.

The term "population of cells" is used to denote a cell population comprising a type of differentiated cells of interest (desired, "target" type of differentiated cells) mixed with at least one other type of cells selected from differentiated cells being different from the target type of differentiated cells, undifferentiated cells and differentiating cells, e.g. progenitor cells. The mixed population of cells may be obtained from a culture of undifferentiated stem cells that have been induced to differentiate thereby forming a cell culture comprising a population of cells at different stages of differentiation. Alternatively, the population of cells may be obtained by transdifferentiation of somatic cells.

The term "target type of differentiated cells" or "target cells" is used herein to denote cells that have differentiated from stem cells and exhibit a cytoskeletal profile that allows the survival of the target cells in a mixed population of cells following treatment of the population with a cytotoxic agent.

The term "cytoskeletal profile" is used to denote the presence or absence in the target type of cells of a pre-identified cytoskeletal component. At times, the profile refers to the presence of a cytoskeletal component on the target type of cells, the cytoskeletal component required for survival of the cells in the mixed cell population following treatment with a cytotoxic agent. In some other cases, the profile refers to the absence of a cytoskeletal component, the absence being required for survival of the cells (lacking the component) in the mixed population following treatment with the cytotoxic agent.

When referring to neural cells as the target type of differentiated cells (being a preferred embodiment of the invention), the population of cells may include the target (desired) neuronal cells as well as cells from which the neural cells differentiate or transdifferentiate. The latter may include cells selected from the group consisting of pluripotent stem cells, neural stem cells (NSCs), neural precursors/progenitors (NPs) (multipotent neural cells) or somatic cells (i.e. in case of transdifferentiation). The neuronal cells are characterized in that all express class III β-tubulin.

In accordance with this particular embodiment, it is noted that tubulins are the building blocks of microtubules the latter being a major cytoskeletal system that plays a key role in cell migration and polarity, facilitating neurite outgrowth, axonogenesis, transport and synaptogenesis.

In mammals, tubulins represent about 10% of the total proteins in the brain. In humans, eight α-tubulin and seven β-tubulin genes have been identified and are differentially distributed in tissues. Neural cells incorporate different types of tubulins according to the specific lineage and state of differentiation. Specific isotypes confer particular properties to the neuronal microtubules which may be of importance during nerve growth.

Microtubule stability is governed by enzymatic activity (e.g., HDAC6), tubulin binding/sequestering proteins (e.g., stathmin) and by the inherent properties of tubulin isoforms. Many cytotoxic agents, including newly synthesized small molecules, are known to affect microtubule stability to an apoptosis inducing degree. Tubacin, a HDAC6 specific inhibitor[10] and belinostat (PXD101) increase microtubule stability and confer apoptosis. Mature neurons have a unique composition of microtubules due to the presence of class III β-tubulin.

Class III β-tubulin is a unique isoform exclusively expressed in mature neurons both in vivo and in vitro. Studies of embryonic brain tissue indicate that this isotype is expressed by terminally differentiating neurons but not by proliferative ones[11]. It has also been shown that cells expressing high levels of class III β-tubulin, such as tumor cells, exhibit resistance to the microtubule-targeting cytotoxic agent paclitaxel[12].

Other cytoskeletal components that may be used in the selection of target differentiated cells in accordance with the invention are intermediate filaments (IF). IFs play roles in scaffolding and structure stabilization. Five major types of IF proteins are currently known to be expressed in mature cells, such as in mature neurons, but many others are expressed at earlier developmental stages and are gradually replaced by the later expressing one[13]. The replacement of the IF proteins, or in other words, their absence from the cells may be used to select from the population of cells only those that have matured (i.e. fully differentiated) and therefore lack the early stage IF proteins. For example, nestin is expressed in the earliest stage of neural development but is suppressed downstream the development[14], vimentin, a typical mesenchymal IF is found also in early stages of neural differentiation and declines with maturation while being replaced by other IF such as alpha-internexin[15]. Thus, the use of an apoptotic inducing agent that targets early stage IF proteins may be used to select for matured neural cells that no longer express these IFs and have therefore become resistant. An example of such an agent is Withferin A. Withferin A is a cytotoxic agent from the family of withanolides which binds to vimentin by covalently modifying a conserved cystein residue[16]. By aggregating vimentin, Withferin A interferes with F-actin and induces apoptosis.

The method of the invention thus employs a selection approach based on differential cytoskeletal components of different cell types in a culture system. The population of cells in the culture prior to treatment may comprise, inter alia, pluripotent stem cells, multipotent stem cells (e.g. neural stem cells (NSCs), neural precursors/progenitors (NPs)) and somatic transdifferentiated cells and the method may select only those cells in the culture that show a define cytoskeletal profile, i.e. the presence or lack of a cytoskeletal component.

In accordance with the invention, the cytoskeletal component allows selectivity of the cells to the cytotoxic agent. The effect of the cytotoxic agent, such as an apoptosis inducing agent may be on cells that lack the cytoskeletal component (the component providing resistance to the agent) or on cells that have the cytoskeletal component (the agent being selective to the component and thus inducing apoptosis only in those cells).

The possibility to select and purify a culture system of fully differentiated cells from a mixed population comprising non-differentiated, differentiating cells (e.g. precursors) and/or other types of differentiated cells has many advantages, as would be appreciated by those versed in the art. For example, transplantation of a mixture of mature and differentiating cells often leads to the development of teratomas or neural tumor formation. In this connection, the inventors have found that upon or following transplantation of populations enriched with, predominantly consisting or consisting essentially only of class III β-tubulin expressing neuronal cells there was minimum or no risk of developing teratoma and/or neural tumor formation by the transplanted cells or risk of having non-neuronal cells within neurons grafted into a living body.

Populations of class III β-tubulin expressing neurons may also be useful for drug discovery, high throughput screening of molecules with various effects including but not limited to neurotoxic effect, neuroprotective effect, electrophysiological effect, differentiation and maturation inducing effect, drug induced teratogenic effect and others.

In accordance with some embodiments, the population of cells is obtained from undifferentiated pluripotent SCs in a culture system that supports the differentiation of the undifferentiated pluripotent SCs to form a mixed cells population enriched with one or more subtypes of neuronal cells that express class III β-tubulin. Neuronal cells include dopaminergic, gabaergic. cholinergic or glutamatergic cells.

As a result of incubation in a culture system that supports the differentiation of the undifferentiated pluripotent SCs, the resulting population may also comprise undesired (regarded contaminating) cells. When the system is induced to differentiate into neuronal cells the population of cells may include undesired cells, such as one or more of glia cells, a myriad of neural and neuronal progenitors, undifferentiated SCs and non-neural cells. This mixed population is then treated in accordance with the invention, with a cytotoxic agent that allows the "purification" of the population to remove any undesired cells.

While referring to neuronal cells, it is appreciated that the stem cells may be induced to differentiation into a variety of other somatic cells. Thus, in the context of the present invention, the term "stem cells" as used herein refers to cells which under suitable conditions are capable of differentiating into other cell types having a particular, specialized function (i.e., "differentiated" cells) while under other suitable conditions are capable of self renewing and remaining in an undifferentiated state as detailed below. A "cell" as used herein refers to a single cell as well as to a population of (i.e. more than one) cells. A cell population may be a pure population comprising one cell type. Alternatively, a cell population may comprise more than one cell type. As noted above, the stem cells may be, in accordance with the present invention, pluripotent stem cells as well as multipotent stem cells.

The term "pluripotent stem cells" as used herein, refer to stem cells which can give rise to any differentiated cell types in an embryo or an adult, preferably including germ cells (sperm and eggs) as well as pluripotent stem cells obtained by in vitro techniques known in the art.

Pluripotent SCs express biological markers which are used to identify pluripotent SCs as well as to verify that the cells in the culture are maintained in an undifferentiated state[17][18][19]. A non-limiting list of such cell markers comprise stage-specific embryonic antigens such as SSEA-3 and SSEA-4; antibodies to specific extracellular matrix molecule which are synthesized by undifferentiated pluripotent SC, such as TRA-1-60, TRA-1-81, and GCTM-2; elevated expression of alkaline phosphatase, which is associated with undifferentiated pluripotent SCs; and transcription factors unique to pluripotent SCs and which are essential for establishment and maintenance of undifferentiated SCs, such as OCT-4, Nanog[20].

In some embodiments, the cells may also be identified by the lack of expression of markers that are typically present on differentiated cells. For example, markers that are present in neuronal lineages and will not be present in pluripotent cells include, PSA-NCAM (marker for neural cell); FGF-5 (related to early ectodermal differentiation of neural precursors); PAX-6 and nestin; 3CB2 (markers for radial glia/neural stem) β-III tubulin (marker of neurons) and thyrosine hydroxylase (TH), (markers for dopaminergic), GABA (marker for gabaergic) and glutamate (marker for glutamaergic); and enlagraid-1 (En-1) (the co-expression of which with TH being a marker for midbrain dopaminergic neurons).

Pluripotent SCs can be obtained using well-known cell-culture methods. For example, pluripotent stem cells may be obtained by inducing reprogramming of somatic cells and are referred here as "induced pluripotent stem (iPS) cells". Induced pluripotent stem cells are derived from somatic cells by various means, including, but not limited to, forced expression of transcription factors, growth factors, small molecules, and others, that reprogram the somatic cell to become pluripotent stem cells[21][22][23].

The pluripotent stem cells are, in accordance with some preferred embodiments, embryonic stem (ES) cells. "Embryonic stem cell" or "pluripotent embryonic stem cell", which are also referred to as an "ESC" are pluripotent cells obtained from embryonic tissue formed after fertilization, parthenogenetic activation, and somatic cell nuclear transfer. The ESC may be developed from human blastocysts, morulas, cleavage stage embryos or blastomeres or from embryonic germ (EG) cells obtained from the genital tissue of a fetus any time during gestation, preferably before 10 weeks of gestation. Pluripotent stem cells can also be obtained from the human gonad after birth for example from human testis.

Human blastocysts are typically obtained from human preimplantation embryos, from in vitro fertilized (IVF) oocytes, parthenogenetically activated oocytes or following somatic cell nuclear transfer. Alternatively, a human embryo single cell can be expanded to the cleavage stage, morula or blastocyst stage. For the isolation of human ESC from blastocysts, most commonly the zona pellucida is removed from the blastocyst. The whole blastocyst may be used to derive stem cells or alternatively, the inner cell mass (ICM) is isolated by immunosurgery, in which the trophectoderm cells are lysed and removed from the intact ICM by gentle pipetting. The ICM may be isolated by any alternative method including mechanical methods or with the assistance of laser[24]. The ICM, blastomeres or whole intact blastocyte is then plated in a tissue culture flask containing the appropriate medium which enables its outgrowth. Following 9 to 15 days, the outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 1-2 weeks. For further details on methods of preparation human ES cells[25-27].

Commercially available human ES cells (hESCs) can also be used in accordance with the invention. hESCs can be purchased from the NIH human embryonic stem cells registry. Non-limiting examples of commercially available embryonic stem cell lines are BG01, BG02, BG03, BG04, CY12, CY30, CY92, CY10, TE03 and TE32.

In accordance with some other embodiments, the population of cells is obtained by transdifferentiation of somatic cells, for example, mouse and human fibroblasts. Transdifferentation includes forced expression of transcription factors which are converted into functional neurons, for example, dopaminergic neuronal cells[33].

The population of cells obtained by transdifferentiation may comprise the target cells, such as neuronal cells as well as other types of cells. Thus, treatment of the cell population resulting from transdifferentiation with a cytotoxic agent, as disclosed herein, allows the "purification" of the population to remove any undesired cells.

The term "undifferentiated cells" as used herein, refer to stem cells that have the ability to form any adult cell; the term "differentiating cells" as used herein, refer to cells obtained from undifferentiated stem cells but that have not yet matured into fully differentiated cells, e.g. precursor cells; and the term "differentiated cells" as used herein, refer to fully specialized (mature) cells obtained from undifferentiated or differentiating cells.

"Undifferentiated pluripotent SC" are true pluripotent if they: (i) are capable of prolonged (more than 3 weeks, more than 4 weeks and at times even more than 10 weeks) proliferation in vitro in an undifferentiated state; and (ii) are capable of differentiation to derivatives of all three embryonic germ layers (endoderm, mesoderm, and ectoderm) even after prolonged culture. Human ES cells (hES cells) are derived from fertilized embryos that are less than one week old (in the cleavage or blastocyte stage) or produced by artificial means (such as by nuclear transfer) that have equivalent characteristics. In some embodiments, the undifferentiated pluripotent SC are Undifferentiated Pluripotent iPS cells" or "Undifferentiated ESC", having the above characteristics.

"Multipotent stem cells" are stem cells which are capable of giving rise to many, but limited, number of cell types. For example, a hematopoietic stem cell can give rise to several types of blood cells but not into brain cells or other types of cells. When referring to the selection of neural cells, the stem cells in the mixed population may comprise neural stem cells (NSC) and neural precursors (NP), which may be derived from pluripotent stem cell or from the brain of aborted fetuses or from the post natal brain at any age.

Various methods for directing differentiation of undifferentiated stem cells are known in the art and all are equally applicable for forming a mixed population in accordance with the method of the invention.

Also, it is appreciated that the mixed population of cells may be available commercially and therefore be purchased for use in the method of the invention.

A variety of culture systems are known in the art to promote specific differentiation of stem cells to a specifically desired population of somatic cells. For example only and without being limited thereto, a culture system that supports the directed differentiation of SCs into neural precursor cells may comprise a basic medium supplemented by FGF2 and/or noggin, as described, for example by Itsykson, P., et al.[28]. Further, for example, a culture system that supports the directed differentiation into dopaminergic neuronal cells initially comprises a medium supporting differentiation into neural precursor cells, which are in turn directed into dopaminergic neuronal cells by the supplementation of the medium with at least one of sonic hedgehog (SHH), purmorphamine (an activator of the SHH signaling), fibroblast growth factor (FGF), or a member of the Wnt family.

In one embodiment, the basic medium in supporting stem cell differentiating into somatic cells is selected from Neurobasal™ (Gibco, Invitrogen cell culture, USA Cat. No. 21103-049 1998/1999), DMEM-F12 (Gibco, Invitrogen cell culture, USA Cat. No. 11320-033), Cellgro Stem Cell Growth Medium (Cat No. 2001 CellGenix Germany 2005), KO-DMEM (Cat. No, 10829-018 Gibco 1998/1999) and X-Vivo 10 (Cat. No. 04-380Q Lonza Switzerland 2007). Most preferably the present invention makes use of DMEM-F12 as the basic medium (i.e. the basic media consists essentially of DMEM-F12). DMEM-F12 is known in the art of cell cultures and is commercially available.

The culture medium may be further supplemented by other components known to be used in cell cultures, such as and without being limited thereto:

N2 supplement (Gibco-Invitrogen)
B27 supplement (Gibco-Invitrogen)
a member of FGF family (e.g. FGF2);
extracellular matrix (ECM) component (e.g. fibronectin, laminin, collagen and gelatin);
antibacterial agents (e.g. penicillin and streptomycin);
non-essential amino acids (NEAA);
Ascorbic acid
neurotrophin (e.g. GDNF, BDNF, NT3, NT4). The neutrophins are known to play a role in promoting the survival of SCs in culture);
Nicotinamide (NA) known to assist in the prevention of differentiation of cells into extraembryonic lineages and in the maintenance of the cells in undifferentiated state, as well as to promote the cells' survival and proliferation (WO 03/104444));
Bone morphogenic protein (BMP) antagonist. It is noted that under culture conditions that support undifferentiated proliferation of hESCs noggin (a BMP antagonist) prevents extraembryonic background differentiation of hESCs. While under conditions that promote differentiation, noggin is known to prevent the differentiation to non-neural lineages, favoring the differentiation to a neural fate. The BMP antagonist may be selected from, without being limited thereto, noggin, chordin, or gremlin.

Depending on the specific composition of the culture system, the nature of the SC-derived population may be a priori determined. In other words, the undifferentiated SCs may be induced to differentiate into a specific and pre-selected fate. To this end, the undifferentiated SCs are cultivated in a culture system comprising a medium that directs differentiation to a specifically desired population of somatic cells, thereby providing a population of cells highly enriched for a specific cell type (desirably, a pure population of cells of a single type). A variety of essentially single type somatic cell populations may be derived from undifferentiated SCs and those versed in the art will know how to select the medium components and establish the desired differentiation inducing culture system which directs the specific differentiation of the latter to the desired population of somatic cells.

For example and without being limited thereto, directing differentiation of undifferentiated and pluripotent SCs to neural precursor cells or neural stem cells may be obtained by cultivating the SCs in a differentiation inducing culture medium comprising DMEM/F12 medium (Gibco) supplemented with B27 (1%, Gibco) (DMEM/F12/B27 medium), FGF-2 (20 ng/ml) and noggin (750 ng/m, R&D Systems, Inc., Minneapolis, Minn.) as exemplified herein below and also by Itsykson, P., et al.[28], or by Reubinoff et al.[29].

Further, for example, directing differentiation of SCs to midbrain dopamineric neuronal cells may be obtained by first inducing differentiation into neural precursor cells, such as described above, followed by cultivation of the neural precursor cells in a basic medium, such as DMEM/F12/B27 medium supplemented with at least one of fibroblast growth factor, preferably fibroblast growth factor 8 (FGF8) and sonic hedgehog (SHH), a member of the Wnt family, preferably Wnt 1, as exemplified below and also described by Kim T E et al.[30]. Co-culture with cells that promote midbrain differentiation such as the PA6 stromal cells, or midbrain astrocytes may be also used.

The resulting cells may be further differentiated into midbrain dopaminergic neurons in the presence of one or more of a member of the Wnt family, such as, Wnt5a, at least one or more of an FGF, such as FGF20, and any one of dibutyryl cyclic AMP (dbCAMP), glial cell derived neurotrophic factor (GDNF), transforming growth factor β3 (TGFβ3), ascorbic acid, Neurotrophin 3 and 4 (NT3 and NT4).

Further as an example, the undifferentiated and pluripotent SC may be directed to differentiate into any other sub-type of peripheral or central nervous system neurons or glia cells including, without being limited thereto, gabaergic and glutamaergic neurons, first by inducing differentiation into neural precursor cells, such as described above, followed by cultivation of the neural precursor cells in a basic medium, such as DMEM/F12/B27 medium supplemented with differentiation inducing factors and survival promoting factors such as ascorbic acid, NT3 and NT4.

The differentiation of the stem cells results in the population of cells comprising the desired cells, namely, those exhibiting the pre-defined cytoskeletal profile, and undesired cells, the elimination of which is desired.

The term "undesired cell(s)" is used to denote any cell whether other than the target type of cells and includes a single cell or in an aggregation/cluster of cells, the undesired cell lacking the pre-identified cytoskeletal profile. As indicated above, the pre-identified profile is required for the selective survival and separation of a specific type (the "target type") of differentiated cells (i.e. cells of interest) from other types of differentiated cells in the population and/or from cells in the population at earlier stages of differentiation (e.g. from their precursors).

Such undesired cell(s) may interfere with the function of the differentiated cells in both in vitro and in vivo applications. For example, the undesired cells may result in, or cause a disease, disorder or pathological condition in a subject following cell transplantation, as discussed above.

When starting from undifferentiated SC, these may be incubated for several hours, preferably one day and at times even several days, e.g. a week to obtain a mixed population of cells comprising at least the target type of differentiated cells. For example, the thus obtained, mixed population of cells, may comprise neuronal cells among other types of cells. The cells in the culture system are then refreshed with the same or different culture medium (the "refreshing medium"). For the purpose of maintaining only the desired, "target type" (e.g. neuronal cells), the refreshing medium is then supplemented with an amount of the cytotoxic agent. In the case of neuronal cells, the cytotoxic agent is an apoptosis inducing agent, e.g. microtubule stabilizing agent. The amount of the agent is sufficient to induce apoptosis in cells that are lacking the desired profile.

A "cytotoxic agent", in the context of the present invention, is an agent that when brought into contact with the cells in the mixed population, it causes death of only cells lacking the pre-identified profile (e.g. expressing or lacking the pre-identified cytoskeletal component that confer, respectively, resistance or sensitivity to this agent). The death may be programmed cell death, namely, apoptosis, or death as a result of necrosis.

In one embodiment, the cytotoxic agent is an apoptosis inducing agent, namely, an agent that induces cell death only in cells expressing or lacking the pre-identified cytoskeletal component that confer, respectively, resistance or sensitivity to this agent.

One preferred example of an apoptosis inducing agent is a microtubule stabilizing agent. A microtubule stabilizing agent is any agent that binds to a cytoskeletal component of a cell type and thereby inhibits or prevents mitotic division of these cells. Microtubule stabilization may be as a result of binding of the agent to a tubulin isotope specific to a cell type; an effect on enzymatic activity, sequestration of proteins, etc. As indicated above, neural microtubules differ spatially and temporally in the type of tubulins that they incorporate and specific isotopes confer particular properties to the neuronal microtubules.

Numerous microtubule-targeting agents currently approved or in clinical development, include the taxanes, such as paclitaxel, docetaxel, vinblastine, vincristine, colchicines, combretastatin, epothilones and taccalonolides which are plant-derived compounds.

Another example of cytoskeleton-based apoptosis inducing agent is withaferin A that targets the intermediate filament vimentin. Cells gradually replace vimentin with internexin and neurofilaments, and thereby become insensitive to the apoptosis inducing agent, withaferin A. Similarly, cardiomyocytes stop expressing vimentin upon final differentiation and thus expected to show resistance to withaferin A, allowing the selection of differentiated cells from mixed cultures.

Yet other cytoskeletal components may be cytokeratins expressed in epithelial cells. Phorboxazoles A and B that have a tumor growth arrest activity, as well as their synthetic analogs were shown to bind cdk4 to cytokeratins and prevent the translocation of cdk4 to the nucleus. This caused the arrest of cell cycle progression[31]. Thus, cells which do not express cytokeratins may not be affected by the cytotoxic agent and his is used, in accordance with the invention, to select and isolate non-epithelial cells in mixed cultures.

Incubation with the cytotoxic agent, such as microtubule-targeting agent is for a time period and in an amount sufficient to modify the mixed cell population. When the agent is a microtubule-targeting agent, the time and amount are sufficient to modify a population comprising neuronal cells to cause death (eliminate) cells that do not express class III β-tubulin and thus not resistant to the treatment with microtubule targeting agent. These cells that do not express class III β-tubulin are typically non-neuronal cells. In this particular example, the selected cells in the modified population of cells are those expressing the desired and pre-identified cytoskeletal component which confers resistance to microtubule-targeting agent (i.e., class III β-tubulin). In other words, the modified neuronal population is enriched for the target cytoskeletal component, thus resistant to the treatment with the microtubule targeting agent.

The time period and amount of the cytotoxic agent required to affect modification of the cell population is determined by morphological assessment for absence of rosettes and undifferentiated colonies in live cultures and by detection of markers for mature cells vs. markers for earlier progenitors (e.g. class III β-tubulin, vs. nestin and Otx2 when directing differentiation to neural cells) in equivalent samples. Apoptotic and/or necrotic cell numbers will also be determined by standard methods (e.g. annexin V, propidium iodide inclusion) at different time points and with different amounts of the agent. Typically, incubation with the apoptosis inducing agent would be for several hours. In one embodiment, the time of incubation with the agent is between 12 hours to 48 hours.

Once the modified cell population is obtained the cytotoxic agent is removed, i.e. the medium is replaced with a fresh medium so as to allow recovery and enrichment of the modified cell population suitable for transplantation or other applications.

In one embodiment, the apoptosis inducing agent is paclitaxel and the modified population of cells comprising predominantly only dopaminergic neurons.

The resulting cell population comprising predominantly cells of the desired profile, e.g. expressing the pre-defined cytoskeletal parameters, such as class III β-tubulin, may be used, for instance, for preventing the in situ development, following transplantation, of undesired populations of cells. Undesired population of cells may include, without being limited thereto, rosette structures (i.e., a typical rounded colony of early neural progenitors, with or without a lumen) and flat clusters of undifferentiated pluripotent stem cells. The rosette structure may include, without being limited thereto, teratoma and bulky neural tumor masses.

The term "population (of cells) comprising predominantly" which is used herein interchangeably with "population (of cells) consisting essentially of" is used to denote a population wherein at least 90%, at times 95%, at time even 99% or even 100% of the cells exhibit the pre-identified and desired cytoskeletal profile. The term "essentially" in this context denotes that no undesired cells are detected in the culture by means acceptable and available in the art. In one embodiment, the modified cell population comprises 100% of the cells exhibit the pre-identified and desired cytoskeletal profile or in other words, does not detect the presence of cells that do not exhibit the pre-identified and desired cytoskeletal profile (using conventional techniques). The present disclosure also provides a cell culture consisting of a target type differentiated cells produced by in vitro treatment of a population of mixed cells with a cytotoxic agent, and preferably an apoptosis inducing agent selective to a pre-identified cytoskeletal profile characterizing (as explained herein) the target type of differentiated cells, the population of mixed cells comprising the target type of differentiated cells and at least one cell selected from the group consisting of undifferentiated cells, differentiating cells (e.g. progenitor cells) and differentiated cells being different from the target type of differentiated cells.

During the different incubation stages, culture media may be refreshed at least every 2-3 days and most preferably at least every 2 days. Further, it is appreciated that the different stages may comprise different media replacements, e.g. at times only the replacement of the basic medium, and at other time points, the replacement of the basic medium comprising one or more of the supplements.

It is also appreciated that as a result of cells expansion, the cells may proliferate into large clusters. Thus, cell manipulations may be performed so as to disaggregate the big clusters of cells. The essentially disaggregated cells may then be transferred to suitable tissue culture carriers (e.g. dishes, culture tubes, culture bioreactors, etc.) for continued expansion.

It is appreciated that certain features disclosed herein, which are, for clarity, described in the context of separate embodiments, may also be provided in combination in a single embodiment. Conversely, various features of the present disclosure, which are, for brevity, described in the context of a single embodiment, may also be provided separately or in any suitable sub-combination.

Although the present disclosure has been described in conjunction with specific embodiments thereof, it is evident that many alternatives, modifications and variations will be apparent to those skilled in the art.

All publications, patents and patent applications mentioned in this specification are herein incorporated in their entirety by reference into the specification.

As used in the specification and claims, the forms "a", "an" and "the" include singular as well as plural references unless the context clearly dictates otherwise. For example, the term "a stem cell" includes one or more stem cells and the term "stem cells" includes one stem cell as well as more than one stem cell.

As used herein, the term "or" means one or a combination of two or more of the listed choices.

Further, as used herein, the term "comprising" is intended to mean that the methods and culture systems includes the recited elements, but does not exclude others. Similarly, "consisting essentially of" is used to define methods and systems that include the recited elements but exclude other elements that may have an essential significance on the functionality of the culture systems of the inventions. For example, a culture system consisting essentially of a basic medium and medium supplements will not include or will include only insignificant amounts (amounts that will have an insignificant effect on the propagation of cells in the culture system) of other substances that have an effect on cells in a culture. Also, a system consisting essentially of the elements as defined herein would not exclude trace contaminants. "Consisting of" shall mean excluding more than trace amounts of other elements. Embodiments defined by each of these transition terms are within the scope of this invention.

Further, all numerical values, e.g., concentration or dose or ranges thereof, are approximations which are varied (+) or (−) by up to 20%, at times by up to 10%, from the stated values. It is to be understood, even if not always explicitly stated that all numerical designations are preceded by the term "about". It also is to be understood, although not always explicitly stated, that the reagents described herein are merely exemplary and that equivalents of such are known in the art.

NON-LIMITING EXAMPLES

Materials and Methods

Cells and Reagents:

hES1, human embryonic stem cell line[10] (included in the NIH registry), Primary human foreskin fibroblasts (passage 17-21) (Mitomycin C-treated) used as feeders for hES1 cells. Laminin 1 (Trevigen, USA), Poly-D-lysine (Sigma), Paclitaxel (Sigma and EMD, USA), basic FGF, FGF8, SHH, BDNF, GDNF, TGFβ3, NT4 (Peprotech Asia, Rehovot, Israel).

Antibodies:

Tuj1 (mouse mAb, Sigma, or rabbit monoclonal—Covance, N.J., USA), Tyrosine Hydroxylase (rabbit polyclonal, Pelfreeze, Ark., USA), nestin (rabbit polyclonal, Millipore, Mass., USA).

Induction of Neural Differentiation:

hES1 colonies grown on HFF feeders in DMEM supplemented with knockout (KO) serum replacement, PenStrep, non-essential amino-acids and glutamine (Invitrogen, USA), were enzymatically detached by collagenase. Intact colonies were transferred to non-adhesive culture plates to form neurospheres in NSC medium (DMEM-F12 medium, N2, B27, PenStrep and Glutamine) supplemented with noggin (Peprotech Asia, Rehovot, Israel) and 20 ng/ml bFGF. Spheres were grown for 3-5 weeks in suspension, collected, triturated and plated on 10 μg laminin/poly-D-lysine-coated coverslips in NSC medium supplemented with FGF8 and SHH for 6-8-days. At this stage, cells were treated with the appropriate concentrations of paclitaxel for 18-24 hours. Paclitaxel was then removed and cells were allowed to recuperate and continue with the differentiation process for additional 6-8 days in NSC medium with BDNF, GDNF, TGFβ3, NT4, cAMP, ascorbic acid.

Alternatively, cells at the end of the differentiation process—the cells are grown as spheres in suspension for 3-5 weeks and 2 more weeks as adherent culture: 1 week FGF8/SHH+1 week factors) are subjected to paclitaxel treatment.

Paclitaxel Treatment:

Paclitaxel was added to cells at 2 ranges of concentrations of 0.2-20 nM and 100-500 nM. Cells are incubated at 37° C., in 5% $CO_2$, 5% $O_2$. Incubation times vary between 2 hours and 48 hours.

Withaferin A Treatment:

Withaferin A (WTA) 0.5-2 μM is added to cells for 4-24 hours at 37° C., in 5% $CO_2$, 5% $O_2$.

Medium is then removed and cells are washed with PBS (with Ca and Mg).

Cells are either incubated in growth medium for recovery overnight or harvested immediately after removal of WTA.

Cell rounding serves as the initial morphological indication for the onset of apoptosis and general cell viability is determined by Trypan Blue exclusion.

Cell Transplantation:

6-Hydroxydopamine (8 μg/rat) was stereotaxically injected (in a 4 μL solution) into the right substantia nigra of male Sprague-Dawley rats weighing 250-280 g; coordinates of injection: P=4.8, L=1.7, H=−8.6 from bregma. Fourteen days after 6-hydroxydopamine injection, rats were selected for transplantation if they had >350 rotations per hour after s.c. injection of apomorphine (25 mg/100 g body weight) (apomorphine being injected after 14 days) and, if 2 days later (after apomorphine injection) they also had >360 (mean 520±38) rotations per hour after i.p. injection of D-amphetamine (4 mg/kg).

Two to five days later (after the D-amphetamine injection), differentiated hESC that were induced according to the above specified protocols, either paclitaxel-treated or control-treated (DMSO), were detached with collagenase and were transplanted, 400,000 cells in 12 μL/animal along two tracts per striatum (coordinates: antero-medial tract, A=1, L=2, H=−7.5 to −4; posterio-lateral tract, A−P=0, L=3.5, H=−7.5 to −4.5). All rats received daily i.p. injections of 10 mg cyclosporine A per kg (Sandimmune; Novartis, Basel, Switzerland).

Brain Immunohistochemistry:

Rats were euthanized by overdose of pentobarbital and perfused with 4% paraformaldehyde saline. Serial 8 μm coronal frozen sections were prepared. Immunofluorescent staining was performed using the following primary antibodies: Human nuclear antigen (HNA), tyrosine hydroxylase (TH), nestin and diamidino-2-phenylinodole (DAPI). Secondary antibodies Donkey anti-mouse IgG Alexa 488-conjugated or Rhodamine RedX-conjugated, Donkey anti-rabbit IgG Alexa 488 conjugated (Jackson Immunoresearch-) were used according to the primary antibody species.

Results

The above basic protocol for generation of dopaminergic (DA) neurons from pluripotent cells was developed[28][32][29] and uses chemically defined culture conditions for the controlled conversion of hESCs, initially into uncommitted neural precursors. This protocol was used here to obtain a population enriched for DA neurons of mid-brain phenotype. At the end of the differentiation period the culture contained neuronal population with 20-30% DA neurons, glia cells and a myriad of neural and neuronal progenitors. Despite the prolonged differentiation period, a minute number of undifferentiated hESCs persisted which maintains high proliferative capacity. Similarly, a small number of very early and proliferative neural progenitors existed in the heterogeneous cultures. These two populations under proper nourishing conditions (i.e., in-vivo brain tissue) expanded rapidly and formed teratomas and bulky neural tumor masses.

By treatment of the population at the end of the differentiation period with paclitaxel, the elimination of both undifferentiated hES cell colonies as well as highly proliferative early neural progenitors was possible. The in vitro studies demonstrated that following treatment with paclitaxel, the population of cells that express markers of early neural progenitors such as nestin declined, while the cultures were enriched with neurons that express class III β tubulin.

FIGS. 1A-1C show that undifferentiated cells as well as early neural progenitors that typically form rosette structures undergo apoptosis after treatment with paclitaxel (FIGS. 1A and 1B), whereas mature cells with typical neuronal morphology are unaffected by the treatment (FIG. 1C).

The effect of paclitaxel treatment on a mixture of a typical culture comprised of a mixture of neurons and NPs is shown in FIGS. 2A-2D. As shown in FIGS. 2A and 2B, the mixed culture expressed neurons and NPs as indicated by the positive staining of β-III tubulin, which is a neuronal marker (FIG. 2A showing neurons) and of nestin, which is a marker of NPs (FIG. 2B; showing NPs). The effect of paclitaxel treatment on a similar culture is shown in FIGS. 2C and 2D, indicating that the cell culture is enriched for β-III tubulin expressing cells (FIG. 2C), but has a reduced number of nestin-positive cells (FIG. 2D).

These results support the hypothesis that non-neuronal cells are considerably affected by paclitaxel, whereas mature neurons that express class III β-tubulin are more resistant.

The in-vitro results indicate that the proposed method for selection, based on the resistance of class III β tubulin-expressing neuronal cells to the apoptotic induction by paclitaxel, is effective in eliminating non-neuronal cells including undifferentiated stem cells and neural progenitor cells which give rise to tumors in vivo.

These results were further supported by in vivo studies, where the efficient removal of tumor-forming cells in the animal model of Parkinsonian rats (6-OH dopamine-lesioned rats) was evaluated. Paclitaxel-treated cells and untreated cells were transplanted into rat brains. Out of 9 animals which were transplanted with cell preparations treated with 20-50 nM paclitaxel, none developed tumors, while all 6 control animals which were transplanted with untreated cells developed large tumors, 5-8 weeks post transplantation. As shown in FIGS. 3A-3F, animals transplanted with paclitaxel-treated cell preparations did not develop any kind of tumor, as the neuronal graft of paclitaxel-treated cells that was observed in the transplanted striatum, showed no evidence for tumor formation (FIGS. 3D-3F). In contrast, animals transplanted with untreated cell preparations developed tumor masses of different sizes at the site of transplantation (FIGS. 3A-3C). Tumor cells expressed specific human nuclear antigen (HNA) indicating their human origin (FIGS. 3A, 3D), the early neuronal progenitor marker nestin (FIGS. 3B, 3E) and were further stained with diamidino-2-phenylinodole (DAPI) to label total nuclei (FIGS. 3B, 3D).

Figure 4B:
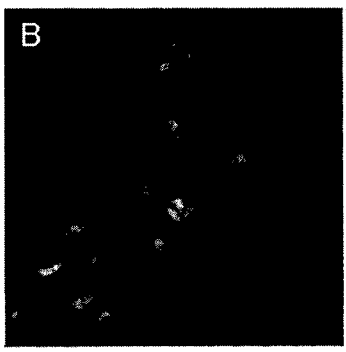
Figure 4C:
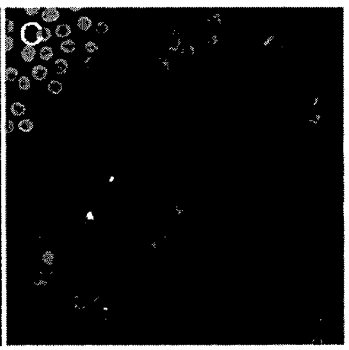

The results in FIGS. 4A-4C further show that paclitaxel-treated grafted cells, marked by human nuclear antigen (FIG. 4B), express tyrosine hydroxylase (FIG. 4A), a marker of dopaminergic neurons. Counterstaining of nuclei with DAPI is presented in FIG. 4C. Thus dopaminergic neurons that were resistant to paclitaxel-treatment in vitro were successfully engrafted into the brain of the Parkinsonian rats.

Collectively, the in vivo results show that the proposed method for selection, based on the resistance of class III β tubulin-expressing neuronal cells, could eliminate tumor forming cells, while the desired neuronal cells, and more specifically dopaminergic neuronal cells were successfully transplanted post selection.

REFERENCES

1. Amariglio, N., et al., *Donor-derived brain tumor following neural stem cell transplantation in an ataxia telangiectasia patient*. PLoS Med, 2009. 6(2): p. e1000029.
2. Cho, M. S., et al., *Highly efficient and large-scale generation of functional dopamine neurons from human embryonic stem cells*. Proc Natl Acad Sci USA, 2008. 105(9): p. 3392-7.
3. Hedlund, E., et al., *Selection of embryonic stem cell-derived enhanced green fluorescent protein positive dopamine neurons using the tyrosine hydroxylase promoter is confounded by reporter gene expression in immature cell populations*. Stem Cells, 2007. 25(5): p. 1126-35.
4. Iacovitti, L., et al., *A protocol for the differentiation of human embryonic stem cells into dopaminergic neurons using only chemically defined human additives: Studies in vitro and in vivo*. Brain Res, 2007. 1127(1): p. 19-25.
5. Lee, H., et al., *Directed differentiation and transplantation of human embryonic stem cell-derived motoneurons*. Stem Cells, 2007. 25(8): p. 1931-9.
6. Thinyane, K., et al., *Fate of pre-differentiated mouse embryonic stem cells transplanted in unilaterally 6-hydroxydopamine lesioned rats: histological characterization of the grafted cells*. Brain Res, 2005. 1045(1-2): p. 80-7.
7. Goldman, S. A., et al., *Large stem cell grafts could lead to erroneous interpretations of behavioral results?* Nat Med, 2007. 13(2): p. 118-9.
8. Hedlund, E., et al., *Embryonic stem cell-derived Pitx3-enhanced green fluorescent protein midbrain dopamine neurons survive enrichment by fluorescence-activated cell sorting and function in an animal model of Parkinson's disease*. Stem Cells, 2008. 26(6): p. 1526-36.

9. Cai, J., et al., *The role of Lmx1a in the differentiation of human embryonic stem cells into midbrain dopamine neurons in culture and after transplantation into a Parkinson's disease model.* Stem Cells, 2009. 27(1): p. 220-9.
10. Haggarty, S. J., et al., *Domain-selective small-molecule inhibitor of histone deacetylase 6 (HDAC6)-mediated tubulin deacetylation.* Proc Natl Acad Sci USA, 2003. 100 (8): p. 4389-94.
11. Fanarraga, M. L., J. Avila, and J. C. Zabala, *Expression of unphosphorylated class III beta-tubulin isotype in neuroepithelial cells demonstrates neuroblast commitment and differentiation.* Eur J Neurosci, 1999. 11(2): p. 517-27.
12. Hari, M., et al., *Expression of class III beta-tubulin reduces microtubule assembly and confers resistance to paclitaxel.* Cell Motil Cytoskeleton, 2003. 56(1): p. 45-56.
13. Lariviere, R. C. and J. P. Julien, *Functions of intermediate filaments in neuronal development and disease.* J Neurobiol, 2004. 58(1): p. 131-48.
14. Lendahl, U., L. B. Zimmerman, and R. D. McKay, *CNS stem cells express a new class of intermediate filament protein.* Cell, 1990. 60(4): p. 585-95.
15. Steinert, P. M., L. N. Marekov, and D. A. Parry, *Molecular parameters of type IV alpha-internexin and type IV-type III alpha-internexin-vimentin copolymer intermediate filaments.* J Biol Chem, 1999. 274(3): p. 1657-66.
16. Bargagna-Mohan, P., et al., *The tumor inhibitor and antiangiogenic agent withaferin A targets the intermediate filament protein vimentin.* Chem Biol, 2007. 14(6): p. 623-34.
17. Allegrucci, C. and L. E. Young, *Differences between human embryonic stem cell lines.* Hum Reprod Update, 2007. 13(2): p. 103-20.
18. Noggle, S. A., D. James, and A. H. Brivanlou, *A molecular basis for human embryonic stem cell pluripotency.* Stem Cell Rev, 2005. 1(2): p. 111-8.
19. Deb, K. D., et al., *Embryonic stem cells: from markers to market.* Rejuvenation Res, 2008. 11(1): p. 19-37.
20. Carpenter, M. K., E. Rosier, and M. S. Rao, *Characterization and differentiation of human embryonic stem cells.* Cloning Stem Cells, 2003. 5(1): p. 79-88.
21. Kiskinis, E. and K. Eggan, *Progress toward the clinical application of patient-specific pluripotent stem cells.* J Clin Invest, 2010. 120(1): p. 51-9.
22. Li, W. and S. Ding, *Small molecules that modulate embryonic stem cell fate and somatic cell reprogramming.* Trends Pharmacol Sci, 2010. 31(1): p. 36-45.
23. Shao, L. and W. S. Wu, *Gene-delivery systems for iPS cell generation.* Expert Opin Biol Ther, 2010. 10(2): p. 231-42.
24. Turetsky, T., et al., *Laser-assisted derivation of human embryonic stem cell lines from IVF embryos after preimplantation genetic diagnosis.* Hum Reprod, 2008. 23(1): p. 46-53.
25. Thomson, J. A. and V. S. Marshall, *Primate embryonic stem cells.* Curr Top Dev Biol, 1998. 38: p. 133-65.
26. Bongso, A., et al., *Isolation and culture of inner cell mass cells from human blastocysts.* Hum Reprod, 1994. 9(11): p. 2110-7.
27. Klimanskaya, I., et al., *Human embryonic stem cell lines derived from single blastomeres.* Nature, 2006. 444(7118): p. 481-5.
28. Itsykson, P., et al., *Derivation of neural precursors from human embryonic stem cells in the presence of noggin.* Mol Cell Neurosci, 2005. 30(1): p. 24-36.
29. Reubinoff, B. E., et al., *Neural progenitors from human embryonic stem cells.* Nat Biotechnol, 2001. 19(12): p. 1134-40.
30. Kim, T. E., et al., *Sonic hedgehog and FGF8 collaborate to induce dopaminergic phenotypes in the Nurr1-overexpressing neural stem cell.* Biochem Biophys Res Commun, 2003. 305(4): p. 1040-8.
31. Forsyth, C. J., et al., *Phorboxazole analogues induce association of cdk4 with extranuclear cytokeratin intermediate filaments.* J Am Chem Soc, 2006. 128(12): p. 3858-9.
32. Cohen, M. A., P. Itsykson, and B. E. Reubinoff, *Neural differentiation of human ES cells.* Curr Protoc Cell Biol, 2007. Chapter 23: p. Unit 23 7.
33. Vierbuchen T, Ostermeier A, Pang Z P, Kokubu Y, Siidhof T C, Wernig M. Direct conversion of fibroblasts to functional neurons by defined factors. Nature. 2010 Feb. 25; 463(7284):1035-41.

The invention claimed is:

1. A method for obtaining a population of cells, the method comprising:
    providing a population of cells comprising a target type of differentiated cells having a pre-identified cytoskeletal profile and at least one cell selected from the group consisting of undifferentiated cells, differentiating cells and differentiated cells being different from the target type of differentiated cells; and
    incubating the population of cells with a cytotoxic agent selective to a pre-identified cytoskeletal profile characterizing the target type of differentiated cells, in an amount and for a time period effective to selectively provide a modified population of cells being enriched with the target type of differentiated cells,
    wherein the modified population comprises at least 90% of the target type of differentiated cells, and
    wherein when transplanted into a subject, the modified population of cells do not develop rosette structures.

2. The method of claim 1, wherein the population of cells comprises neural cells, and neuronal cells.

3. The method of claim 1, wherein the pre-identified cytoskeletal profile comprises presence of tubulin on the target type of differentiated cells.

4. The method of claim 3, wherein the tubulin is class III β-tubulin present on the target type of differentiated cells.

5. The method of claim 3, wherein the cytotoxic agent is paclitaxel.

6. The method of claim 1, wherein the population of cells is obtained from stem cells that are incubated with a culture medium that promotes differentiation into the target type of differentiated cells to form the population of cells.

7. The method of claim 1, wherein the population of cells is obtained from somatic cells that are induced to transdifferentiate into the target type of differentiated cells to form the population of cells.

8. The method of claim 1, wherein the modified population of cells comprises at least 95% differentiated cells.

9. The method of claim 8, wherein the modified population of cells comprises essentially 100% differentiated cells.

10. The method of claim 1, wherein said modified population of cells comprises dopaminergic neurons.

* * * * *